United States Patent
Buchner et al.

(10) Patent No.: US 9,719,890 B2
(45) Date of Patent: Aug. 1, 2017

(54) MICRO-SAMPLING FOR AQUATIC CHEMICAL ANALYSIS

(71) Applicant: BiOMICom Incorporated, Allison Park, PA (US)

(72) Inventors: James D Buchner, Pittsburgh, PA (US); Ross C Willoughby, Pittsburgh, PA (US)

(73) Assignee: BIOMICOM INCORPORATED, Allison Park, PA (US)

( * ) Notice: Subject to any disclaimer, the term of this patent is extended or adjusted under 35 U.S.C. 154(b) by 702 days.

(21) Appl. No.: 13/901,569

(22) Filed: May 24, 2013

(65) Prior Publication Data

US 2014/0349328 A1 Nov. 27, 2014
US 2017/0097286 A9 Apr. 6, 2017

Related U.S. Application Data

(60) Provisional application No. 61/688,884, filed on May 24, 2012.

(51) Int. Cl.
*G01N 1/00* (2006.01)
*G01N 1/20* (2006.01)

(52) U.S. Cl.
CPC .................... *G01N 1/20* (2013.01)

(58) Field of Classification Search
CPC ......... G01N 33/569; G01N 2001/1031; G01N 2001/1093; G01N 33/497; G01N 1/2202;
(Continued)

(56) References Cited

U.S. PATENT DOCUMENTS 5,473,952 A * 12/1995 Lieberman ............... G01N 1/12
73/863.01
5,808,300 A 9/1998 Caprioli
(Continued)

OTHER PUBLICATIONS

Travis S. Elsdon, Sean D. Connell; "Spatial and temporal monitorining of coastal water quality: refining the way we consider, gather and interpret patterns", vol. 5: 157-166, Aquatic Biology, 2009.*

(Continued)

*Primary Examiner* — Nina Bhat
(74) *Attorney, Agent, or Firm* — The Webb Law Firm

(57) ABSTRACT

The current invention describes in vivo and vitro (cultured) sampling technologies that allow direct temporal and spatial sampling from living ecosystems such as those associated with marine ecology. The optional use of parallel sampling methods, observatory design, provides for the ability to measure the response of individual organisms to a variety of both biotic and abiotic stresses. Sampling in small volumes and close proximity to living organisms has allowed direct measurement of various invertebrate and other aquatic species in marine ecosystems. These sampling techniques are intended to apply to any liquid based ecosystem in an attempt to minimize sampling as a dependent variable in measuring the chemical and biological behavior of the ecosystem. If is intended that this sampling technology be used to directly measure the chemical behavior of a wide variety of organisms; including, plants, animals, and microorganisms (e.g. algae, plankton). These probes facilitate the direct measurement of metabolism, decomposition, pollution, and stress or stimuli from the local environment. A variety of sampling tips and probes have been developed for discrete and continuous sampling. A variety of sampling probe geometries, sizes, and sampling capabilities are disclosed that enable both contact and non-contact sampling of (Continued)

the chemical environment. The liquid sampling has been optimized for chemical analysis with liquid chromatography mass spectrometry. Fatty acid and lipid profiling have been demonstrated on a number of species from a cultured aquatic using these techniques.

45 Claims, 9 Drawing Sheets

(58) Field of Classification Search
CPC . G01N 2001/2285; G01N 1/14; G01C 13/006
USPC ......... 73/1.43, 53.01, 64.56, 170.29; 422/70, 422/82.05, 82.06, 89
See application file for complete search history.

(56) References Cited

U.S. PATENT DOCUMENTS

| | | | | |
|---|---|---|---|---|
| 5,993,649 | A * | 11/1999 | DeBusk | C02F 3/32 210/103 |
| 6,561,046 | B1 * | 5/2003 | Taylor | G01N 1/14 73/863.23 |
| 6,998,249 | B1 * | 2/2006 | McKim | G01N 33/5014 435/29 |
| 7,442,927 | B2 | 10/2008 | Fedorov | |
| 7,767,880 | B2 * | 8/2010 | McGrath | A61K 49/0008 424/9.2 |
| 7,831,075 | B2 | 11/2010 | Wilson et al. | |
| 9,188,512 | B2 * | 11/2015 | Van Mooy | G01N 1/10 |
| 2002/0164274 | A1 * | 11/2002 | Haggett | A61L 2/025 422/128 |
| 2004/0261143 | A1 * | 12/2004 | Mumm | A01K 67/0275 800/20 |
| 2007/0031962 | A1 * | 2/2007 | Levin | G01N 33/5088 435/288.5 |
| 2007/0218457 | A1 * | 9/2007 | McKim | G01N 33/5014 435/4 |
| 2009/0026092 | A1 * | 1/2009 | Reardon | C12Q 1/002 205/778 |
| 2009/0221014 | A1 * | 9/2009 | Reardon | C12Q 1/002 435/18 |
| 2013/0244250 | A1 * | 9/2013 | Yang | C07K 14/43595 435/7.1 |
| 2013/0298702 | A1 * | 11/2013 | Lam | G01N 1/14 73/863.23 |
| 2016/0212978 | A1 * | 7/2016 | Matthews, III | A01K 61/002 |

OTHER PUBLICATIONS

Boardman et al., "The interface of an array of five cappilaries with an array of one-nanoliter wells for high-resolution electrophoretic analysis as an approach to high-throughput chemical cytometry", Anal. Chem., 2008, pp. 7631-7634, vol. 80, No. 19.

Gong et al., "On-line Sample Preconcentration Using Field-amplified Stacking Injection in Microchip Capillary Electrophoresis", Anal. Chem., 2006, pp. 3730-3737, vol. 78, No. 11.

Hu et al., "Asymmetry between Sister Cells in a Cancer Cell Line Revealed by Chemical Cytometry", Anal. Chem., 2004, pp. 3864-3866, vol. 76.

Jung et al., "Thousandfold signal increase using field-amplified sample stacking for on-chip electrophoresis", Electrophoresis, 2003, pp. 3476-3483, vol. 24.

Wang et al., "Direct Sampling from Human Liver Tissue Cross-sections for Electrophoretic Analysis of Doxorubicin", Anal. Chem., 2009, pp. 3321-3328, vol. 81, No. 9.

\* cited by examiner

| Patent Component | Alternatives |
|---|---|
| Interaction | 1. Abiotic<br>    a. pH<br>    b. temperature<br>    c. chemistry profiles<br>    d. pollutants<br>2. Biotic<br>    a. Anti-predation; repellants & escape substances<br>    b. mediation of spatial competition; venoms<br>    c. Suppressants & antibiotics<br>    d. Inductants; facilitation of reproduction<br>    e. Counteractants; neutralization and antifouling<br>    f. Attractants; food and food location signals<br>    g. Signals for danger or toxicity<br>    h. Stimulants; products inducing growth in the receiver |
| Target organisms | 1. Marine invertebrates; individuals, populations, communities, ecosystem<br>2. Bacterial colonies; sediment<br>3. Bacteria; free water<br>4. Marine vertebrates |
| Sample introduction means | 1. Diffusible compounds with direct capillary<br>2. Contact transfer with permeable membranes<br>3. Sample concentration with selective extraction methods<br>4. Bethnic pore water for bacterial input/output<br>5. Purgeable, extractable, or ionic species |
| Monitoring means | 1. Chromatographic; gas, liquid, and electrophoretic methods<br>2. Absorption and emission spectroscopy<br>3. Electrochemical<br>4. Wet chemical<br>5. Complex sensor arrays combining physicochemical and physiologic data to produce information pertaining to chemical ecology |

Fig1

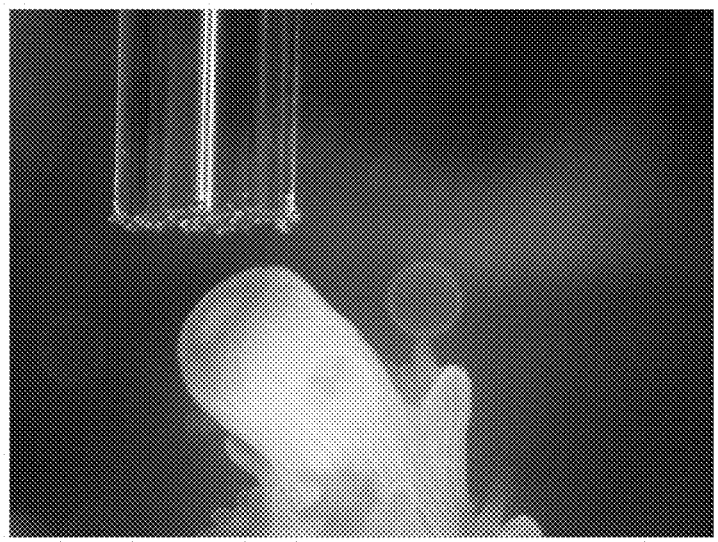
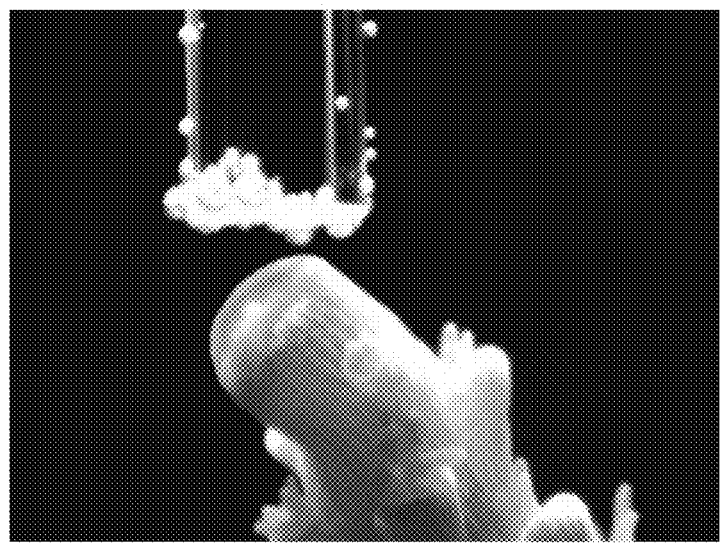
Fig 4

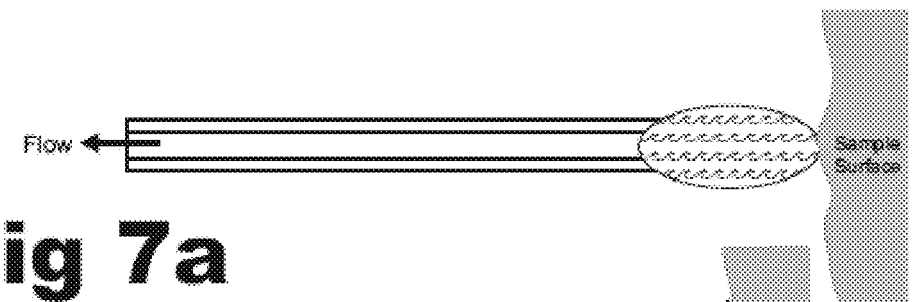
Fig 7a
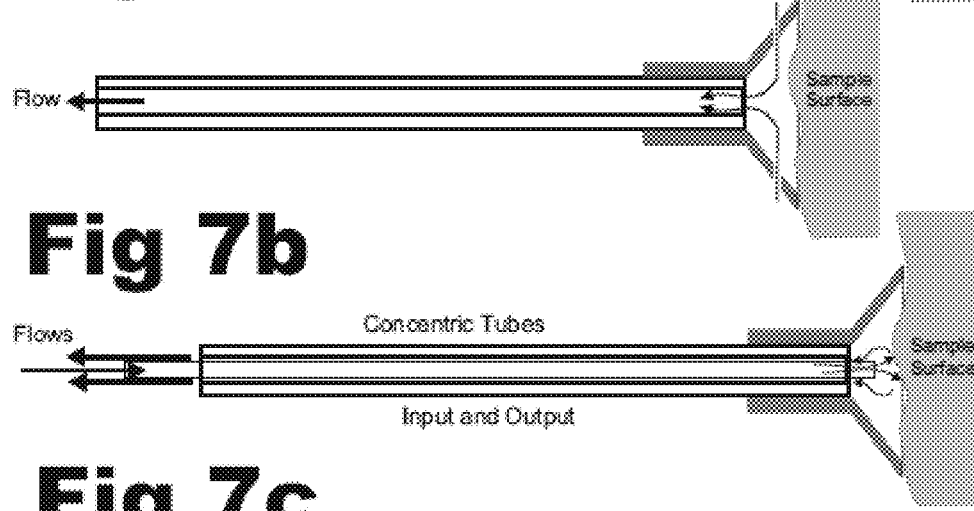
Fig 7b
Fig 7c
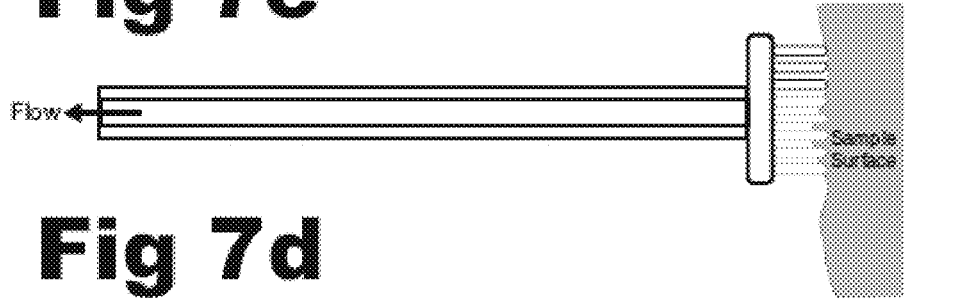
Fig 7d

MICRO-SAMPLING FOR AQUATIC CHEMICAL ANALYSIS

CROSS-REFERENCES

This application is entitled to the benefits of Provisional Patent Application Ser. No. 61/631,050 filed on Dec. 27, 2011, now Nonprovisional patent application Ser. No. 13/728,865, and Provisional Patent Application Ser. No. 61/688,884, filed on May 24, 2012.

FIELD OF INVENTION

This invention pertains to the chemical and bio-molecular testing and control of cellular behavior to characterize composition and production of chemical species from biological activities, particularly those activities pertaining to aquatic or marine ecosystems.

BACKGROUND OF THE INVENTION

The primary method for studying marine ecosystems for evaluation of chemical ecology is to harvest and sacrifice the biological species before analysis. Although these techniques (we term blender chemistry) provide rich chemical information from biological systems, they lose information in the process by stressing the sampled organisms and potentially changing measured components. In addition, sampling techniques prior to this fail to provide adequate spatial and temporal information to capture communication between species via semiochemical release (chemical ecology). This requires much higher spatial resolution, temporal resolution, and feedback with the organism in a viable ecosystem while sampling to ensure the environmental or behavioral conditions haven't changed. Blender chemistry simply provides an integration of sample components and loses much of the valuable temporal and spatial components of biological behavior. In addition, significant sensitivity enhancement is required to measure many of the trace metabolites and semiochemicals that end up diluted when using blender methods. The prior technologies fail to sample in time windows that capture measurable amounts of sample before being diluted into an essentially infinite reservoir of liquid (e.g. the ocean).

DESCRIPTION OF FIGURES

FIG. 1—Table indicating selected Interaction Parameters, Target Organisms, Sample Introduction Means, and Monitoring Means for use with the current invention. The invention is intended to allow spatial and temporal measurements of the interaction of biotic and abiotic components of a living ecosystem, whereby the chemical interaction, products of metabolism, and behavior of the organism can be monitored and measured. The items on this list are intended to represent examples of measurement parameters but are not intended to limit the application of the present invention in scope. The aquatic ecosystem is controlled by adjusting the composition of the environment that sample organisms reside in order to study cause of effect. (e.g., add pollutants, add nutrients, add non-chemical stimuli such as specific light wavelengths).

FIG. 4—A photograph of a simple tubular sample probe (600 um) performing non-contact sampling of a microfeature (polyp) of an acropora. Note the collection of respiratory gases from the organism on the sample probe tip.

FIG. 7—Embodiments of contact sampling probes intended to interrogate the chemical composition of surface attached sample components at various organism surfaces or physical features; showing a) a swab tipped probe intended to make contact with the sample organism without damage to the surface of the organism, b) a conical tipped probe made of either soft or hard material with radial holes intended to sample a radius of surface defined by the tip geometry from the sample organism, c) a conical tipped probe similar to b) without radial holes, said conical tipped probe conducting liquid to the sample to sweep the surface and collecting sample containing liquid through a coaxial outlet tube as indicated by the arrows, and d) a brush tipped (soft or hard brush) to agitate sample surface to dislodge sample material for subsequent collection through the outlet of the tube.

DESCRIPTION OF INVENTION

The current invention describes devices (sampling and analysis arrangements) and methods intended to monitor (and additionally) measure the behavior of selected in vivo or in vitro aquatic organisms; including, plants, animal, and micro-organisms. The Table presented in FIG. 1 is intended to itemize examples of the types of behavior and environmental conditions that serve as parameters of interest in studying marine ecosystems. A measurement platform for observing the marine species includes the ecosystem and the device. The device is intended to measure species specific biomolecules as a function of experimental conditions during in vitro experiments, or species specific biomolecules as function environmental conditions during in vivo experiments. The present invention allows the measurement of biochemical products of biological activity. Monitoring the interaction of living organisms requires the measurement of both biotic and abiotic parameters within the observation regions.

The invention comprises one or more methods for direct sampling in vivo or in vitro marine ecosystems that comprise:
  a sample or plurality of samples,
  a means for sampling,
  a means for collecting samples,
  a means for monitoring sample organism for position and behavior to optimize
  sampling position and time,
  a means for positioning said sampling means,
  a means for conditioning sample,
  a means for enriching sample components,
  a means for analyzing said sample components,
whereby the sampling of the said sample is controlled both spatially and temporally in by in order to characterize and relate chemical and physical behavior of biological organisms within a given ecosystem. A representative number of sample organisms, interactions from the ecosystem, sample introduction means, and monitoring means are itemized in FIG. 1. It is a primary objective of the present invention to monitor the biotic and abiotic interactions at the organism, organism sub-feature, or cellular level. Monitoring the experimental conditions for the devise may include one or more video, chemical, optical, or physical measurement in order to correlate behavior relating to experimental or environmental conditions. Cultured ecosystems have an advantage of allowing the experimenter to more fully control the environmental conditions and composition, both abiotic and biotic.

Preferred Embodiment

Figure 2:
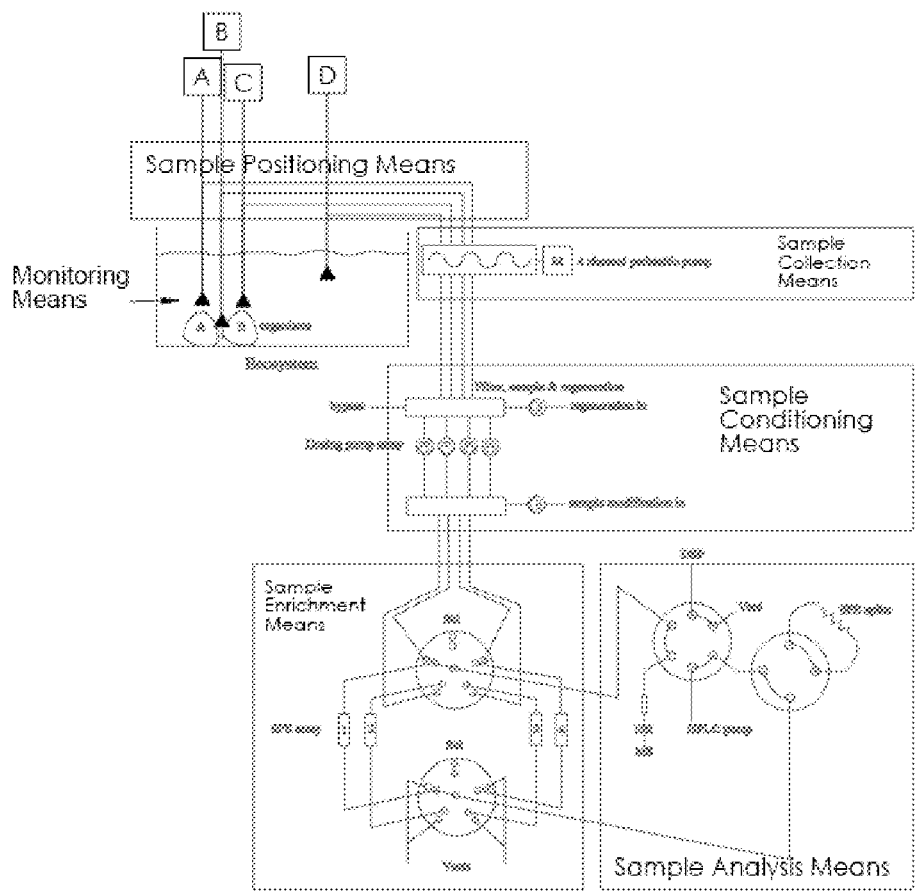
FIG. 2—Flow diagram of the major components of a aquatic sampling system. These components comprise a plurality of sampling probes labeled A through D, a sample positioning means for adjusting the position of sample probes relative to the sampled organism, a sample collection means to control the sampling time and volume (in this embodiment a peristaltic pump with multiple sampling streams), a sample conditioning means (filters, salt washes, addition of buffers), a sample enrichment means (this case a solid phase extraction means to isolate and enrich sample components), a sample analysis means (in this case a liquid chromatographic column with gradient separation conditions interfaced to a mass spectrometer). Also required for effective operation of the sampling system is a variety of switching and control devices to facilitate the discrete processes of sampling, enriching, conditioning, separating and analyzing components.

A preferred embodiment is schematically illustrated in FIG. 2. The cultured marine ecosystem is schematically represented as an aquarium tank containing species A and B. Four sample probes are inserted into the tank at various observation positions relative to the observed species. One probe at organism A, one at organism B, one at the interface between the two species, and one in the background as a control measurement. Each sample probe (A through D) can be manually or automatically positioned by a sample positioning means. The temporal and spatial position of each sample probe can be fixed or movable depending on the nature of the experiment, one alternative embodiment of this invention used a monitoring means to observe the conditions of both sample and observed organism. For example, the monitoring means are capable of monitoring movement of the observed species and automatically changing sample probe position relative to sample organism. All four probes can be discretely and/or simultaneously sampled by a peristaltic pump which serves as a collection means. The sample streams are collected and delivered for analysis. A wide variety of sample conditioning means, sample enrichment means, and sample analysis means are integrated into the system for sample pre-treatment, filtering, and pH adjustment. The conditioned sampling lines are each delivered to a solid phase extraction column where sample can be enriched, and desalted. The sample enrichment means of SPE provided for enriched sample to be delivered to an analysis means comprising liquid chromatography mass spectrometry.

This embodiment utilizes a number for switch valve in the conditioning, enrichment, and analysis phases of analysis to enable sample loading, unloading, elution, and regeneration with clean solvents to prevent carryover between samples. Valve also allow switch from sample to sample stream, and sample to sample time (same sample stream, different time). Sample volumes and sampling durations can be varied to accommodate sampling requirements.

This invention utilizes monitoring means for measuring one or more of the following attributes of the sample ecosystem;
  a) monitoring the position and spacing of sampling probes relative to sampled organism or region,
  b) monitoring the visual appearance of organisms in various states of health or under various states of behavior (e.g. feeding, preying, reproducing, defending),
  c) monitoring a organism specific response such as fluorescence or emission,
  d) monitoring the background levels or populations of biotic materials (e.g. algae, plankton)
  e) monitoring the background levels abiotic materials (e.g. salts, hydronium ions)
  f) monitoring the abiotic parameters (temperature, current, temperature gradients, turbidity).
Monitoring means are intended to be used for the following objectives;

a) feedback information on position or positions of samples relative to sampling probes,
b) feedback information to correlate biochemical results related to monitored parameters,
c) feedback information to correlate biochemical response induced stimuli.

Additional Preferred Embodiments—(Non-Contact Sampling)

Figure 3:
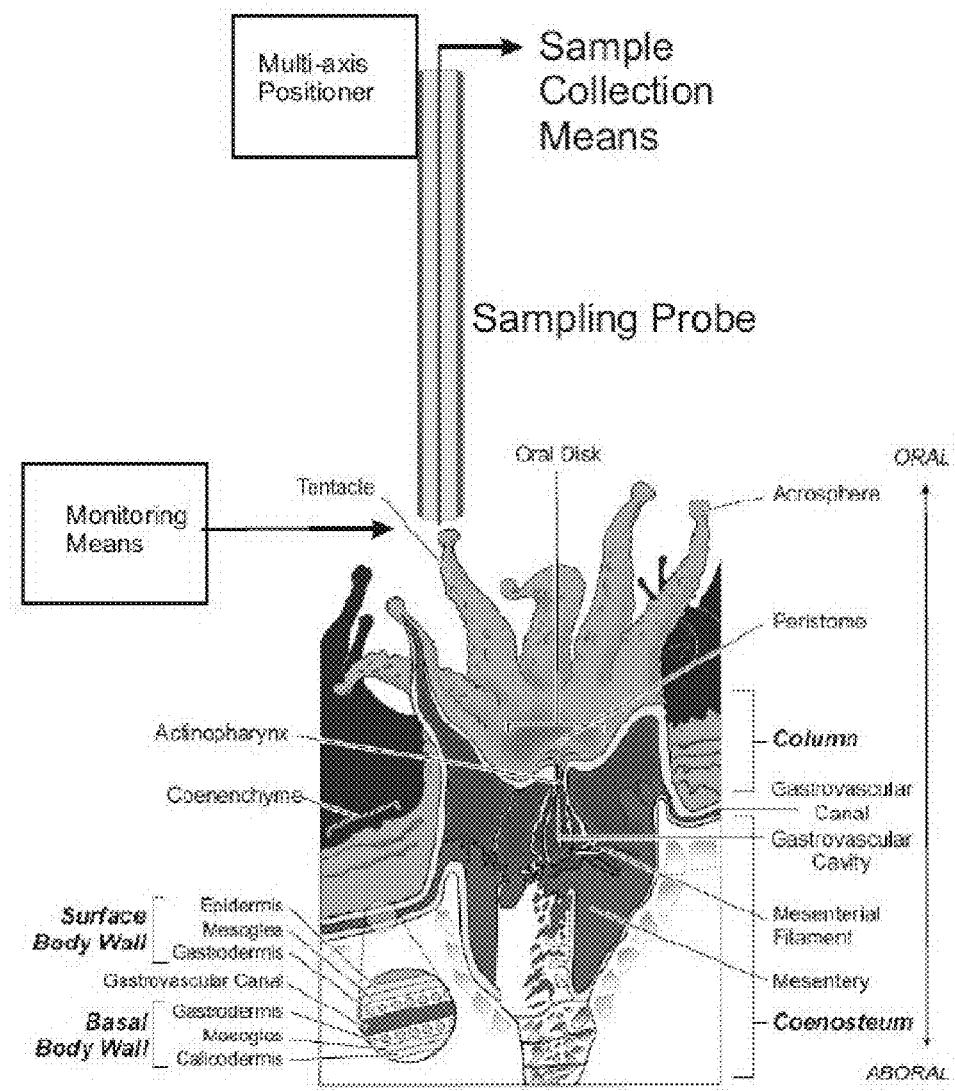
FIG. 3—Schematic diagram of a marine organism showing a tentacle sampling probe designed to milk the tentacles for a wide variety of chemical components or chemical signature of biological condition or response to stimuli. The sampling probe is observed with an external monitoring means and the sampling probe is able to assume an optimal position relative to a moving physical feature of the sampled organism.
Figure 5:
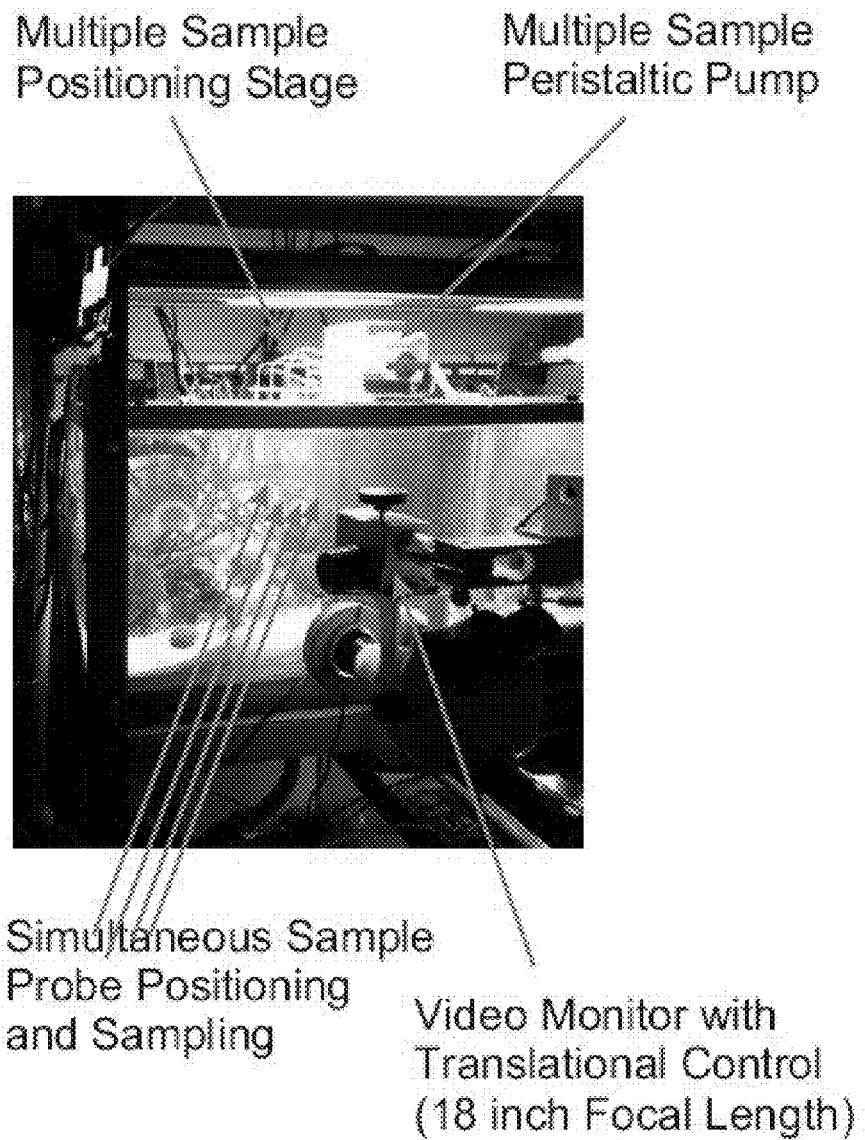
FIG. 5—A photograph of a cultured reef environment with an extended microscopic video camera (in this case with an 18 inch focal length) used to monitor, position, and adjust the position of sampling probes in order to maintain consistent sampling distance, or potentially to protect the organism harm or damage from closely positioned sampling probes. Shown in the photograph are the sample tank containing acropora and other species, a four probe sample positioning apparatus, and a four line peristaltic sampling pump.
Figure 6A:
FIG. 6—Embodiments of non-contact sampling probe geometries intended for various application and types of interactions with sample organisms or sample surfaces; showing a) a simple tubular probe for withdrawing liquid directly from sample regions, b) an angled tubular probe for addressing organism geometries that are more complex or inaccessible with linear probes, c) a fritted or porous tipped probe to collect sample through a higher collection cross-section while preventing particulate material from entering the sampling stream, and d) a blank tipped probe with radial sampling holes oriented around the region near the tip of the probe.
Figure 6B:
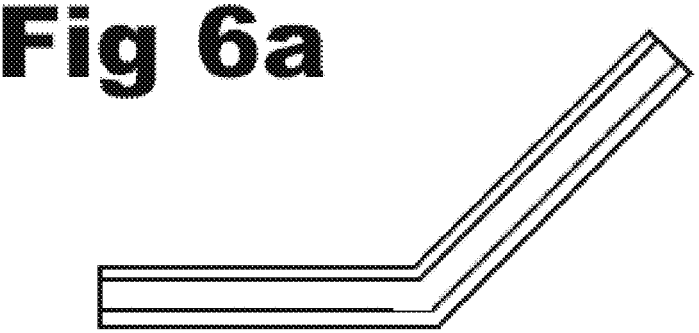
Figure 6C:
Figure 6D:

FIG. 3 illustrates the relationship between sample probe and physical feature of the target organism. This figure shows a tubular sampling probe positioned out the apex of a tentacle in order to collect chemical output from the region of the acrosphere. A monitoring means is used to align the sampling probe with the tentacle. The device is capable of manual or automated alignment. FIG. 4 shows a photograph of sampling probe interaction with an aquatic species of hard coral called acropora. The acropora structure sampled in this experiment was the polyp. Exact positioning of the sampling probe is important to capture species specific molecules associated with the oral grove at the end of the polyp. The probe dimension in this photograph is 600 um diameter. Small species features can be matched with small dimensioned and/or geometrically appropriate probes. FIG. 5 is a photograph of the monitoring means for the present invention whereby organism can be observed with a long focal length (18 inch) microscope that is movable and focusable relative to selected sample species in the tank. A multiple sampling probe holding and positioning assembly is locate above the tank allowing discrete positioning of sample probes relative to sample organisms. Manual or automated control of both monitoring microscope and sample probes is possible.

Embodiments of non-contact sampling probe geometries intended for various applications and types of interactions with sample organisms or sample surfaces are shown in FIG. 6. The example non-contact sampling probes are show as, a) a simple tubular probe for withdrawing liquid directing from sample regions, b) an angled tubular probe for addressing organism geometries that are more complex or inaccessible with linear probes, c) a fritted or porous tipped probe to collect sample through a higher collection cross-section while preventing particulate material from entering the sampling stream, and d) a blank tipped probe with radial sampling holes oriented around the region near the tip of the probe.

These non-contact probes have the advantage of sampling aqueous environments in marine ecosystems without contact in potentially stimulating chemical response from sample organisms. These have particular utility for evaluating extracellular materials for defense response, attractant emission, repellent emission, and products of metabolism.

Additional Preferred Embodiments—Contact Sampling

FIG. 7 illustrate a number of embodiments of contact sampling probe geometries intended for various applications and types of interactions with sample organisms or sample surfaces. These embodiments of contact sampling probes are intended to interrogate the chemical composition of surface attached sample components at various organism surfaces or physical features; showing a) a swab tipped probe intended to make contact with the sample organism without damage to the surface of the organism, b) a conical tipped probe made of either soft or hard material with radial holes intended to sample a radius of surface defined by the tip geometry from the sample organism, c) a conical tipped probe similar to c) without radial holes, sail conical tipped probe conducting liquid to the sample to sweep the surface and collecting sample containing liquid through a coaxial outlet tube as indicated by the arrows, and d) a brush tipped (soft or hard brush) to agitate sample surface to dislodge sample material for subsequent collection through the outlet of the tube.

FIGS. 7a-c are intended to dislodge sample components from the surface and sweep said dislodged sample components into the outlet of the respective sampling tube. The swab-type probe is intended to prevent damage to the surface of the organism while allowing collection of components that are not dissolved in the surrounding ambient water (bulk fluid). Probe 7b and 7c with conical tip allow pseudo sealing of the surface around the cone with the edge of the cone. In FIG. 7b, the ambient water is drawn into the sampling region (inside the cone) to sweep analytes off the surface through simple turbulence. In the case of FIG. 7c, liquid input from the sampling probe is directed at the organism surface and subsequently drawn to the outlet tube for collection and analysis. The sampling cone is made of either soft (flexible) materials or hard depending on the properties of the organism surface being sampled.

One alternative embodiment of FIG. 7c would entail the addition of reagent solutions that are intended to stimulate or react in some way with the sampled organism to induce the output of a chemical response. Products of that response are drawn to the sampling tube and analyzed.

FIG. 7d utilizes the bristles of a brush to agitate components on the sample surface in order to dislodge and entrain components in the liquid flow toward the outlet tube. The bristles are intended to be either soft for sensitive surfaces or hard for dislodging strongly bound components of durable surfaces. This technique would be good for collecting microorganisms as well as chemical species. We envision condition micro-organisms collected from surface or suspended into the ambient water to require special pre-treatment such as cell lysing and isolation of cellular fractions, before chemical analysis.

Additional Preferred Embodiments—(Small Volume of Micro-Sampling)

Figure 8A:
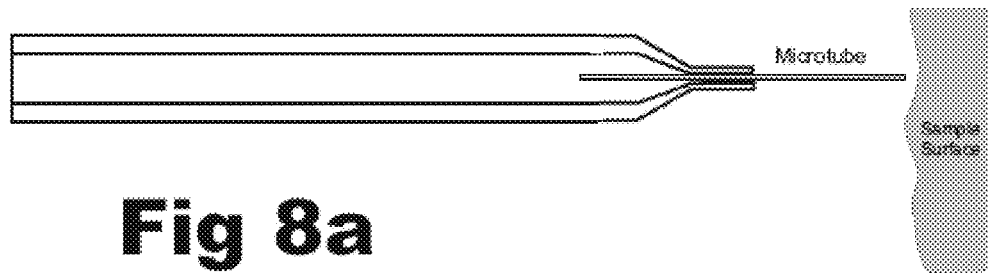
FIG. 8—Embodiments of micro-sampling probes that are intended to extract small volumes of sample at or near the surface of an organism, showing a) a microtube mounted in the tip of a larger transfer tube, b) a microtube mounted in the tip of a larger transfer tube with input or output flow paths for introducing sample collecting liquids to the sample probe and collecting small volumes of sample through the microtube into the higher flow input and output steams, and c) a microtube mounted to a microsyringe to extract discrete sample volumes of sample local the organisms utilizes a micro-switching valve to switch from loading to injection positions.
Figure 8B:
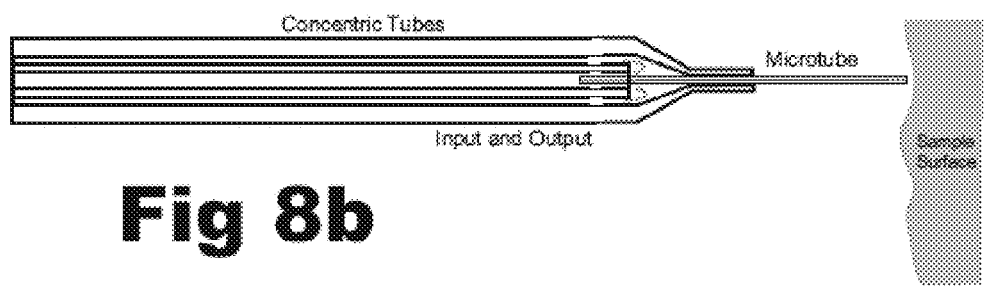

FIG. 8 illustrates a number of embodiments of the sampling probe for sample volumes that are much smaller (100 uL to sub-uL). Many applications of ecosystem analysis require significantly enhanced spatial and temporal resolution to measure bioemmission in short time domains for from small physical regions of the organisms. The present sampling probe embodiments include designs for reduced size tips and reduced volume sampling in order to increase both spatial and temporal resolution. Embodiments of a micro-sampling probes that are intended to extract small volumes of sample at or near the surface of an organism are shown. These include a) a microtube mounted in the tip of a larger transfer tube, b) a microtube mounted in the tip of a larger transfer tube with input or output flow paths for introducing sample collecting liquids to the sample probe and collecting small volumes of sample through the microtube into the higher flow input and output steams, and c) a microtube mounted to a microsyringe to extract discrete sample volumes of sample local the organisms utilizes a micro-switching valve to switch from loading to injection positions.

Figure 8C:
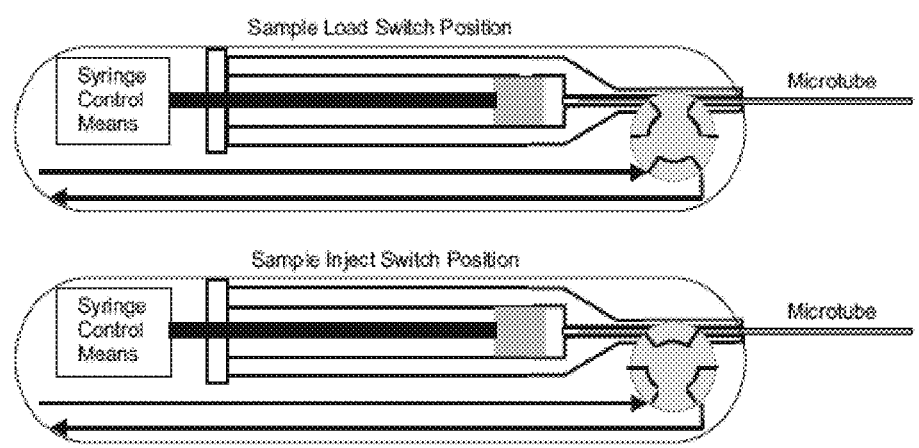
Figure 9A:
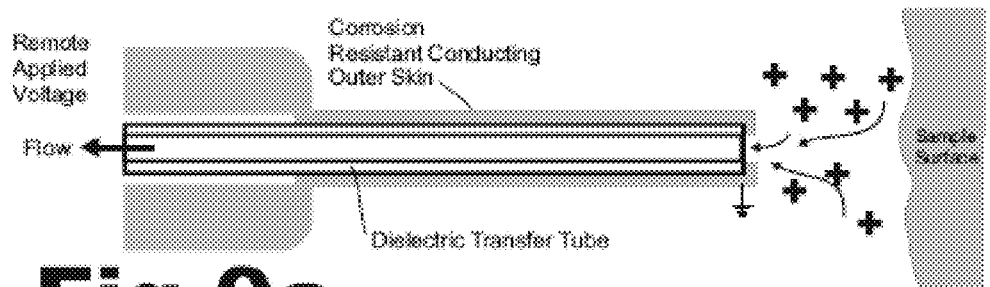
FIG. 9—Embodiments of alternate sampling probes that are intended to selectively extract volumes of sample, showing a) a dielectric tube containing sampling probe sheath by a grounded cover, said dielectric tube having an attractive voltage applied a remote end of the dielectric tube in order to attract ions to and through the tube with a continues field along the length of the dielectric, b) an electrically biased tube insulated from an electrically grounded outer sheath that attracts oppositely charged sample ions to the said biased tube and said charged sample ions are swept into the tube and collected, c) a chemically modified sample probe that allows for the attachment of functional groups that show affinity for selected sample components or provide stimuli to the organism and d) a specialized sampling tip for insertion of sampling tip into sediment to a controlled or metered depth to interrogate species that are associated with subsurface organisms.
Figure 9B:
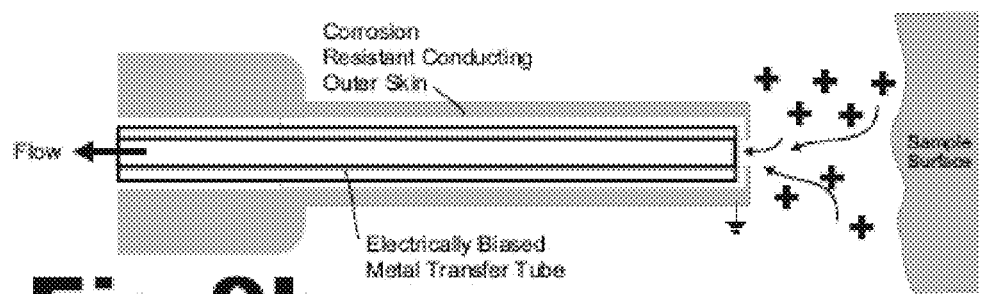
Figure 9C:
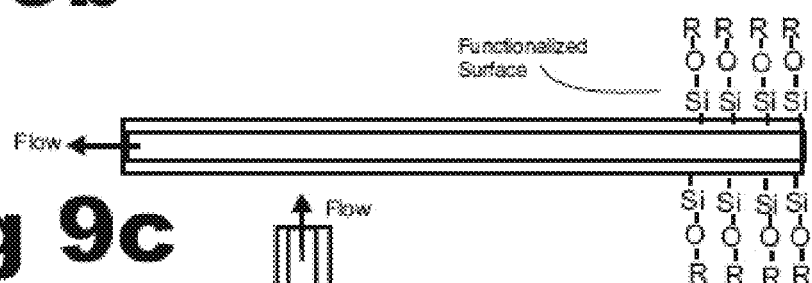
Figure 9D:
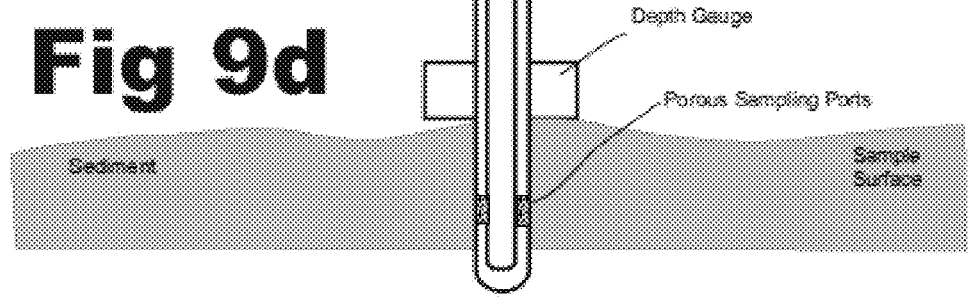

Discrete small volume sampling requires both in FIG. 8c allow small volumes to be collected into a sample loop, injected into a higher flow stream for rapid transmission away from the sampling environment for pseudo-realtime analysis.

Additional Preferred Embodiments—(Specialized Sampling Probes)

FIG. 9 illustrates a number of embodiments of the sampling probe for collecting specific chemical components from the sampled organism or organisms. Embodiments of specialized sampling probes are intended to selectively extract volumes of sample. Embodiments are shown in FIGS. 9a-d, showing a) a dielectric tube containing sampling probe sheath by a grounded cover, said dielectric tube having an attractive voltage applied a remote end of the dielectric tube in order to attract ions to and through the tube with a continues field along the length of the dielectric, b) an electrically biased tube insulated from an electrically grounded outer sheath that attracts oppositely charged sample ions to the said biased tube and said charged sample ions are swept into the tube and collected, c) a chemically modified sample probe that allows for the attachment of functional groups that show affinity for selected sample components, and d) a specialized sampling tip for insertion of sampling tip into sediment to a controlled or metered depth to interrogate species that are associated with subsurface organisms.

Specialized probes are intended to enhance to collection efficiency of selected components, generally at the expense of other components.

CITATIONS (1) U.S. Pat. No. 5,808,300; August 1998; Caprioli, Appl May 1997, 854,040.
(2) Hu K, Ahmadzadeh H, Krylov S N, *Anal Chem* 2004, 76(13), 3864-6.
(3) Boardman A, McQuaide S C, Zhu C, Whitmore C, Lidstrom M E, Dovichi N J, *Anal Chem.* 2008, 80(19), 7631-4.
(4) Wang Y, Hong J, Cressman E N K, Arriaga E A, *Anal Chem.* 2009, 81(9), 3321-8.
(5) U.S. Pat. No. 7,831,075 B2; November 2010; Wilson et al, Appl October 2006, Ser. No. 11/581,995.
(6) U.S. Pat. No. 7,442,927; October 2008; Fedorov, Appl January 2006, Ser. No. 11/336,137.
(7) "Culture of Animal Cells", 6$^{th}$ Edition, R. Ian Freshney, John Wiley & Sons, Inc., 2010, ISBN 978-0-470-52812-9.
(8) Jung B, Bharadwaj R, Santiago J G, *Electrophoresis*, 2003, 24, 3476-83.
(9) Heineman W R, Gong M, Wehmeyer K R, Limbach P A, Arias F, *Anal Chem.* 2006, 78, 3730-7.

The invention claimed is:

1. An aquatic sampling and analysis system for observing a marine species comprising:
   an ecosystem comprising an in vitro ecosystem or an in vivo ecosystem; and
   a sampling and analysis arrangement comprising:
      a plurality of probes for collecting a sample directly from the marine species or from an environment near the marine species;
      a pump in fluid communication with the probes to initiate collection of the sample from one of the probes; and
      an analyzer in fluid communication with the pump to analyze the sample using chemical measurements,
      wherein the sampling and analysis arrangement is configured to take simultaneous samples from probes at different spatial locations.

2. The system of claim 1, wherein the marine species is a marine invertebrate, a bacterial colony, bacteria, or a marine vertebrate.

3. The system of claim 1, further comprising a monitor connected to the probes to view the marine species or the environment near the marine species.

4. The system of claim 3, wherein the monitor is a video monitor.

5. The system of claim 1, wherein a composition of the environment near the marine species is altered by adding pollutants, adding nutrients, or adding non-chemical stimuli to the environment near the marine species, wherein the probes are configured to collect the sample directly from the marine species or from the altered environment near the marine species to study cause and effect.

6. The system of claim 3, further comprising a controller connected to the probes, the controller configured to automatically position one of the probes based on information from the monitor.

7. The system of claim 1, further comprising a controller connected to the probes to allow a user to adjust a position of one of the probes.

8. The system of claim 1, wherein the analyzer is a mass spectrometer.

9. The system of claim 1, wherein the analyzer is configured to perform chromatographic analysis of the sample.

10. The system of claim 1, wherein one of the probes is a non-contact sampling probe.

11. The system of claim 1, wherein one of the probes is a contact sampling probe.

12. The system of claim 1, wherein one of the probes is a micro-sampling probe.

13. The system of claim 1, wherein one of the probes is a specialized sampling probe.

14. The system of claim 1, wherein one of the probes is configured to dislodge the sample from a surface of the marine species to collect the sample.

15. The system of claim 1, wherein one of the probes is made of a porous material configured to collect liquid and prevent collection of particulate material.

16. The system of claim 1, wherein one of the probes is insertable into the marine species to collect the sample.

17. The system of claim 1, wherein the pump is configured to permit multiple sample streams to flow from the pump to the analyzer.

18. The system of claim 1, wherein the analyzer comprises a switch valve, the switch valve configured to prevent cross-contamination of samples fed to the analyzer.

19. The system of claim 1, wherein the sampling and analysis arrangement further comprises a sample conditioning system in fluid communication with the pump and the analyzer, wherein the sample is conditioned by one or multiple sample conditioning stages in the sample conditioning system prior to being delivered to the analyzer, the sample conditioning stages configured to improve compatibility of the sample to analyzer requirements.

20. The system of claim 19, wherein the sample conditioning system comprises a filter for removing particulate matter from the sample.

21. The system of claim 20, wherein the sampling and analysis arrangement further comprises a solid phase extraction column in fluid communication with the filter, wherein the conditioned sample is delivered to the solid phase extraction column.

22. The system of claim 14, wherein the sample conditioning system adds a sample pre-treater or pH adjuster to the sample.

23. The system of claim 4, wherein the video monitor is connected to a controller, wherein the controller is connected to the probes to allow a user to adjust a position of one of the probes, wherein the controller is configured to control and position or activate and deactivate one of the probes based on information from the video monitor, wherein the information from the video monitor comprises a position of the marine species, a behavior of the marine species, or a chemical response of the marine species to previous stimuli.

24. The system of claim 1, wherein one of the probes comprises a tube, wherein the probe comprises a geometry that conforms to an outer geometry of the marine species.

25. The system of claim 1, wherein one of the probes comprises a tip, wherein the tip is perforated radially to restrict suction of part of the marine species from being swept into the probe.

26. The system of claim 1, wherein one of the probes comprises a tip, wherein the tip comprises adsorbent material.

27. The system of claim 1, wherein one of the probes comprises a sampling tube terminating in a tip, wherein the tip comprises a conical shaped sample standoff, where the sampling tube comprises a concentric set of tubes to deliver solution to the environment near the marine species and subsequently to collect samples through the concentric set of tubes.

28. The system of claim 1, wherein one of the probes comprises a tip, wherein the tip comprises a micro-tube to sample small volume or small spatial regions.

29. The system of claim 28, wherein the probe further comprises input and output flow paths for delivery of solvent to a sample surface and for collection of the sample derived from a sample surface region.

30. The system of claim 29, wherein the probe further comprises a syringe for withdrawing small volumes of the sample from the sample surface, wherein the syringe is mechanically actuated at or near the sample surface, wherein the probe further comprises a valve to direct flow to and from the sample surface.

31. The system of claim 1, wherein one of the probes comprises a tip, wherein the tip comprises a micro-tube with applied voltage to attract ionic species to the probe and direct the ionic species to the analyzer.

32. The system of claim 1, wherein one of the probes comprises a tip having a tip surface, wherein the tip comprises a micro-tube with a chemically adsorbent material attached to the tip surface to bind sample material selectively to either remove unwanted material from a collection flow or to bind specific target analytes for subsequent analysis.

33. The system of claim 1, wherein one of the probes comprises a tip, wherein the tip comprises a tip geometry that facilitates insertion into aquatic sediment for collection of the sample at specific gauged depths from a surface of the aquatic sediment.

34. The system of claim 1, wherein the marine species is contained within the ecosystem.

35. The system of claim 34, further comprising an introduction device in communication with the ecosystem to change a control in the ecosystem.

36. The system of claim 35, wherein the control is an abiotic parameter.

37. The system of claim 35, wherein the control is a biotic parameter.

38. The system of claim 35, wherein the probes collect samples before and after the introduction device changes the control in the ecosystem.

39. The system of claim 35, wherein the probes simultaneously collect samples after the introduction device changes the control in the ecosystem.

40. The system of claim 1, wherein the analyzer analyzes the samples substantially in real-time.

41. The system of claim 1, the sample conditioning system is configured to filter, desalt, or pre-treat the collected sample.

42. The system of claim 1, wherein the analyzer comprises a switching valve configured to allow for sequential introduction of samples to the analyzer.

43. The system of claim 1, wherein a plurality of marine species are placed in spatial proximity such as to enable the plurality of probes to collect a sample that captures communication between the plurality of marine species via semiochemical release.

44. The system of claim 1, wherein a composition of the environment near the marine species is altered by changing the pH, temperature, or light of the environment near the marine species, wherein the probes are configured to collect the sample directly from the marine species or from the altered environment near the marine species to study cause and effect.

45. The system of claim 1, wherein the system is configured for observing products of metabolism, decomposition, or response to a stress source for the marine species.

\* \* \* \* \*